US010849500B2

(12) United States Patent
Kraetschmer et al.

(10) Patent No.: US 10,849,500 B2
(45) Date of Patent: Dec. 1, 2020

(54) AUTOMATIC ORIENTATION OF SUBCUTANEOUS ECG IN IMPLANTABLE MONITORING DEVICES

(71) Applicant: BIOTRONIK SE & Co. KG, Berlin (DE)

(72) Inventors: Hannes Kraetschmer, West Linn, OR (US); Jon Peterson, Lake Oswego, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 262 days.

(21) Appl. No.: 15/813,335

(22) Filed: Nov. 15, 2017

(65) Prior Publication Data

US 2018/0168449 A1    Jun. 21, 2018

Related U.S. Application Data

(60) Provisional application No. 62/435,858, filed on Dec. 19, 2016.

(51) Int. Cl.
*A61B 5/00* (2006.01)
*A61B 5/0402* (2006.01)
(Continued)

(52) U.S. Cl.
CPC .......... *A61B 5/0006* (2013.01); *A61B 5/0422* (2013.01); *A61B 5/04028* (2013.01); *A61B 5/067* (2013.01); *A61B 5/076* (2013.01); *A61B 5/686* (2013.01); *A61B 5/721* (2013.01); *A61N 1/3702* (2013.01); *A61N 1/3706* (2013.01);
(Continued)

(58) Field of Classification Search
USPC .................................................. 600/508–509
See application file for complete search history.

(56) References Cited

U.S. PATENT DOCUMENTS

2005/0288600 A1    12/2005  Zhang et al.
2008/0146941 A1*    6/2008  Dala-Krishna .......... A61B 8/12
                                                                600/466
(Continued)

FOREIGN PATENT DOCUMENTS

EP        2 311 368 A1    4/2011
WO     2009036348 A1    3/2009

OTHER PUBLICATIONS

European Search Report and Annex to the European Search Report on European Patent Application No. EP 17 16 4494.1, dated Jun. 22, 2017 (5 pages).

*Primary Examiner* — Nicole F Lavert
(74) *Attorney, Agent, or Firm* — Buchanan Ingersoll & Rooney PC

(57) ABSTRACT

Various embodiments are directed toward a system and method for determining an orientation of an implantable medical device ("IMD") and automatically adjusting a subcutaneous electrocardiogram ("ECG") signal based on the determined orientation. The method can further include tagging generated SECG signals so as to identify whether a SECG signal had been generated from an implantable monitoring device with its first electrode being superior or inferior relative to its second electrode. Further embodiments can include automatically adjusting the orientation of the generated SECG signals to match that of a preferred orientation.

23 Claims, 2 Drawing Sheets

(51) Int. Cl.
  *A61N 1/37*   (2006.01)
  *A61B 5/07*   (2006.01)
  *A61B 5/06*   (2006.01)
  *A61B 5/042*  (2006.01)
  *A61N 1/375*  (2006.01)
  *A61B 5/0452*  (2006.01)

(52) U.S. Cl.
  CPC ............ *A61B 5/0031* (2013.01); *A61B 5/0452* (2013.01); *A61B 2560/0468* (2013.01); *A61B 2562/0219* (2013.01); *A61N 1/3756* (2013.01); *A61N 1/37512* (2017.08)

(56) References Cited

U.S. PATENT DOCUMENTS

| | | | |
|---|---|---|---|
| 2009/0270747 A1 | 10/2009 | van Dam et al. | |
| 2013/0338727 A1* | 12/2013 | Mokelke | A61N 1/3606 607/45 |
| 2015/0032186 A1* | 1/2015 | Cushing | A61N 1/36036 607/57 |

* cited by examiner

AUTOMATIC ORIENTATION OF SUBCUTANEOUS ECG IN IMPLANTABLE MONITORING DEVICES

CROSS-REFERENCE TO RELATED APPLICATIONS

This patent application claims the benefit of U.S. Provisional Patent Application No. 62/435,858, filed on Dec. 19, 2016, which is hereby incorporated by reference in its entirety.

FIELD OF THE INVENTION

Various embodiments are directed toward a system and method for determining an orientation of an implantable monitoring device and automatically adjusting a subcutaneous ECG signal based on the determined orientation.

BACKGROUND OF THE INVENTION

Implantable medical devices ("IMDs") are generally implanted subcutaneously, which may be at the left chest of a patient. IMDs are typically equipped with a first electrode located at one end of the IMD and a second electrode located at an opposite end of the IMD. The electrodes facilitate recordation of subcutaneous electrocardiogram ("SECG") signals. The orientation of an SECG signal, as displayed by a Holter monitor or similar display, can depend on the orientation of the IMD within the body of the patient. For example, if the first electrode is oriented upwards in the body, the orientation of the SECG signal display might match that of the orientation of a traditional surface ECG signal display. Typically, traditional surface ECG signal displays are known and are familiar to medical professionals reviewing such signals. However, if the first electrode is oriented downwards in the body, the orientation of the SECG signal displayed may be inverted (inverted with respect to a SECG signal display obtained when the first electrode is oriented upwards). It may be beneficial to always, or at least have an option to, record and display the SECG signal in an orientation that matches the traditional surface ECG orientation, especially is the physician is unaware of the body orientation of the patient when reading the signals.

The present invention is directed toward overcoming one or more of the above-identified problems.

SUMMARY OF THE INVENTION

The present invention can include a method and a system for utilizing an accelerometer/motion sensor ("AM sensor") to ascertain the orientation of an implantable medical device, which can include, but is not limited to, implantable cardiac pacemakers, implantable defibrillators, implantable nerve stimulators, diaphragm stimulators, etc. A particular implantable medical device is an implantable cardiac monitor ("ICM"). Further embodiments can include adjusting the orientation of a subcutaneous electrocardiogram ("SECG") signal so as to cause it to be displayed with a preferred orientation. To accomplish this, the system can include a processor, a display, an AM sensor, and an IMD. The method can include using the AM sensor to determine the orientation of the IMD, which may further include tagging the generated SECG signal so as to identify whether the SECG signal had been generated from an IMD with its first electrode being superior or inferior relative to its second electrode. Further embodiments can include automatically adjusting the orientation of the generated SECG signal to match that of a preferred orientation.

The utilization of the AM sensor within the IMD can detect the orientation of such an IMD device, and with that, the position of the first electrode relative to a second reference point of the IMD after it has been implanted. The AM sensor can be multi-axis accelerometer/motion sensor used to determine such orientation. Depending on the position of the first electrode relative to the second referent point of the IMD (i.e., the orientation), the SECG signal can be automatically inverted to allow the recording and display of the SECG in a way that matches an orientation of a traditional surface ECG.

Exemplary embodiments may describe the implantable medical device as an ICM; however, it should be understood that any type of implantable medical device can be used without departing from the spirit and scope of the present invention.

In an exemplary embodiment, a method for determining an orientation of implantable medical device ("IMD") after being implanted subcutaneously within a patient to generate subcutaneous electrocardiogram ("SECG") signals, wherein the IMD comprises an attached or incorporated acceleration/motion sensor ("AM sensor"), may include: determining an orientation of the IMD from the AM sensor measuring an elevation or an altitude of at least one first reference point of the IMD relative to an elevation or an altitude of at least one second reference point of the IMD, wherein when the at least one first reference point is superior relative to the at least one second reference point the IMD is in an up-orientation, and when the first reference point is inferior relative to the second reference point the IMD is in a down-orientation; tagging each SECG signal with the ascertained up-orientation or down-orientation; determining a preferred orientation for displaying the SECG signals before the SECG signals are displayed; converting at least one SECG signal to generate a SECG display signal having the preferred orientation; and, displaying the SECG display signal having the preferred orientation. The IMD can further include a first electrode and a second electrode. The first electrode may be located at an end of the IMD that is an opposite end at which the second electrode is located. The at least one first reference point may be associated with the first electrode and the at least one second reference point may be associated with the second electrode. The AM sensor may be a three-axis acceleration/motion sensor. The step of converting the at least one SECG signal to generate the SECG display signal having the preferred orientation can include an inversion function performed on the SECG signal. The method can further include use of at least one of an inclinometer and a gyroscope for the determining the orientation of the IMD. In some embodiments, the IMD is an implantable cardiac monitor ("ICM").

In another exemplary embodiment, a method for determining an orientation of an implantable medical device ("IMD") after being implanted subcutaneously within a patient to generate subcutaneous electrocardiogram ("SECG") signals, wherein the IMD comprising an attached or incorporated acceleration/motion sensor ("AM sensor"), can include: operatively associating a processor and a non-transitory memory with the AM sensor and a display; determining an orientation of the IMD from the AM sensor measuring an elevation or an altitude of at least one first reference point of the IMD relative to an elevation or an altitude of at least one second reference point of the IMD, wherein when the at least one first reference point is superior relative to the at least one second reference point the IMD is in an up-orientation, and when the first reference point is inferior relative to the second reference point the IMD is in a down-orientation; tagging each SECG signal with the ascertained up-orientation or down-orientation; determining a preferred orientation for displaying the SECG signals before the SECG signals are displayed; converting at least one SECG signal to generate a SECG display signal having the preferred orientation; and, displaying the SECG display signal having the preferred orientation. The method can further include associating the up-orientation with a first proxy value and the down-orientation with a second proxy value. The method can further include identifying each up-orientation generated SECG signal as a SECG-1 signal and identifying each down-orientation generated SECG signal as a SECG-2 signal. The step of converting the at least one SECG signal may further include converting at least one of each SECG-1 signal and SECG-2 signal to generate the SECG display signals having the preferred orientation. The step of displaying the SECG display signal can further include sending the SECG display signal to the display. The IMD may have a first electrode and a second electrode. The first electrode may be located at an end of the IMD that is an opposite end at which the second electrode is located. The at least one first reference point may be associated with the first electrode and the at least one second reference point may be associated with the second electrode. The AM sensor may be a three-axis acceleration/motion sensor. The converting the at least one SECG signal to generate the SECG display signal having the preferred orientation can further include an inversion function performed on the SECG signal. The method can further include use of at least one of an inclinometer and a gyroscope for the determining the orientation of the IMD. In some embodiments, the IMD is an implantable cardiac monitor ("ICM").

In another exemplary embodiment, a method for determining an orientation of an implantable medical device ("IMD") after being implanted subcutaneously within a patient to generate subcutaneous electrocardiogram ("SECG") signals, wherein the IMD has an attached or incorporated acceleration/motion sensor ("AM sensor"), a first electrode and a second electrode, wherein the first electrode is located at an end of the IMD that is an opposite end at which the second electrode is located; wherein the AM sensor is a three-axis acceleration/motion sensor capable of communicating with a processor in operative association with a non-transitory memory and a display, the processor programmed to cause the display to display subcutaneous electrocardiogram ("SECG") signals; the method can include determining an orientation of the IMD from the AM sensor measuring an elevation or an altitude of the first electrode relative to an elevation or an altitude of the second electrode, wherein when the first electrode is superior relative to the second electrode the IMD is in an up-orientation and when the first electrode is inferior relative to the second electrode the IMD is in a down-orientation; tagging each SECG signal with the ascertained up-orientation or down-orientation; determining a preferred orientation for displaying the SECG signals before the SECG signals are displayed; converting at least one SECG signal to generate a SECG display signal having the preferred orientation; and, displaying the SECG display signal having the preferred orientation. The method can further include use of at least one of an inclinometer and a gyroscope for the determining the orientation of the IMD. In some embodiments, the IMD is an implantable cardiac monitor ("ICM").

While these potential advantages are made possible by technical solutions offered herein, they are not required to be achieved. The presently disclosed system and method can be implemented to achieve technical advantages, whether or not these potential advantages, individually or in combination, are sought or achieved.

Further features, aspects, objects, advantages, and possible applications of the present invention will become apparent from a study of the exemplary embodiments and examples described below, in combination with the Figures, and the appended claims.

BRIEF DESCRIPTION OF THE DRAWINGS

The above and other objects, aspects, features, advantages and possible applications of the present invention will be more apparent from the following more particular description thereof, presented in conjunction with the following Figures, in which:

FIG. 2A shows the IMD with the first electrode in a superior position relative to the second electrode, FIG. 2B shows the first electrode in a superior position relative to the second electrode but the IMD is seen as being tilted, and FIG. 2C shows the first electrode in an inferior position relative to the second electrode.

DETAILED DESCRIPTION OF THE INVENTION

The following description is of an embodiment(s) presently contemplated for carrying out the present invention. This description is not to be taken in a limiting sense, but is made merely for the purpose of describing the general principles and features of the present invention. The scope of the present invention should be determined with reference to the claims.

The present invention can include a method and a system for utilizing an accelerometer/motion sensor ("AM sensor") to ascertain the orientation of an implantable medical device ("IMD"), which may include an implantable cardiac monitor ("ICM"). Further embodiments can include adjusting the orientation of a subcutaneous electrocardiogram ("SECG") signal so as to cause it to be displayed with a preferred orientation.

Figure 1:
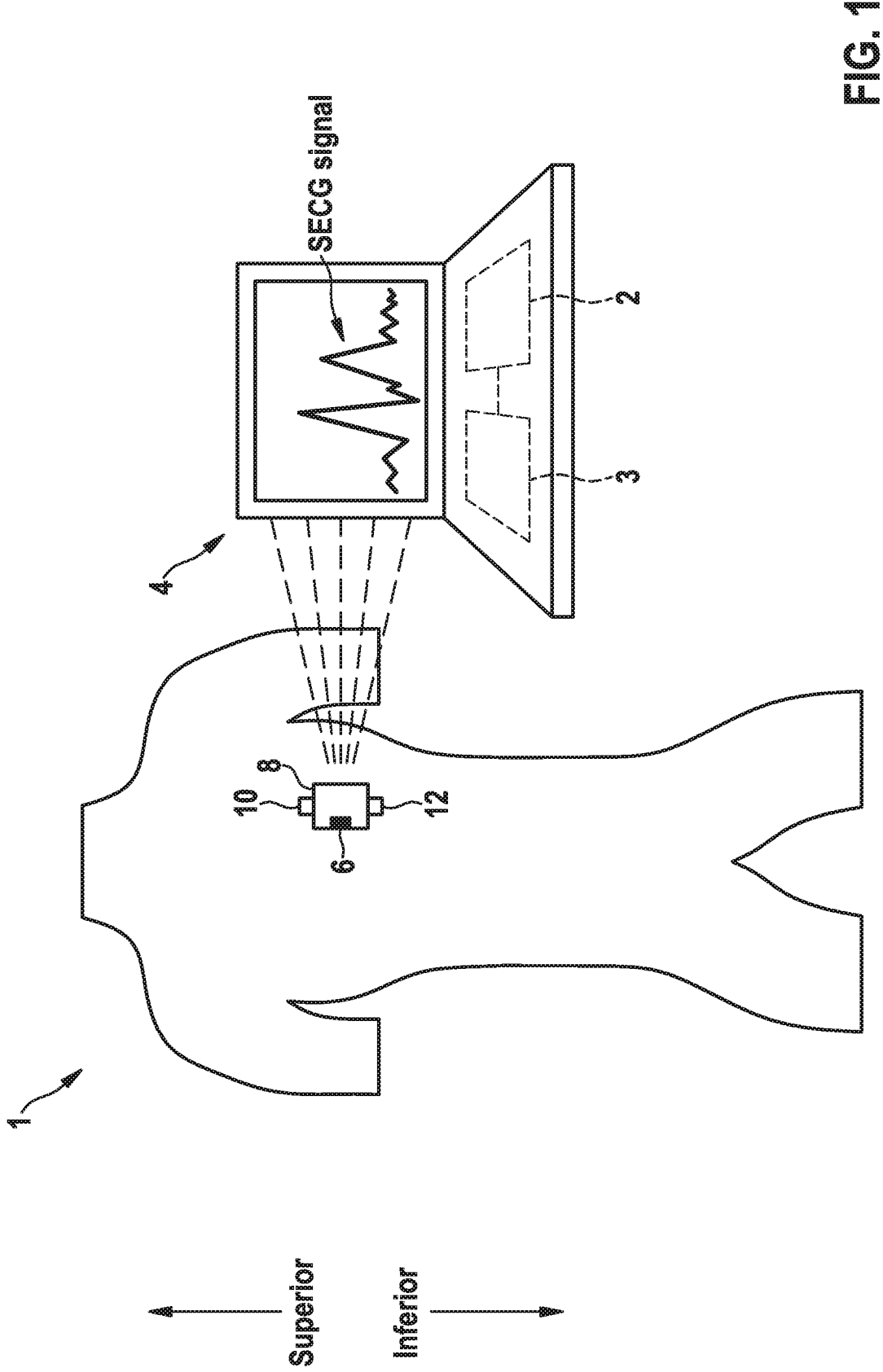
FIG. 1 shows the system being used in accordance with an embodiment of the method to generate SECG signals in a preferred orientation via a display.

Referring to FIG. 1, the system 1 can include a processor 2, a display 4, an AM sensor 6, and an IMD 8. The method can include using the AM sensor 6 to determine the orientation of the IMD 8. The method can further include tagging the generated SECG signal so as to identify whether the SECG signal had been generated from an IMD 8 with its first electrode 10 being superior or inferior relative to its second electrode 12. The method can further include automatically adjusting the orientation of the generated SECG signal to match that of a preferred orientation.

The IMD 8 can include a first electrode 10 positioned at a first end of the IMD 8 and a second electrode 12 positioned at a second end of the IMD 8. The electrodes 10, 12 may facilitate recordation of subcutaneous electrocardiogram ("SECG") signals. As noted above, the orientation of an SECG signal, as displayed by a Holter monitor or similar display 4, can depend on an orientation of the IMD 8. For example, if the first electrode 10 is at a higher elevation or altitude relative to the second electrode 12, then the SECG signal generated from the IMD 8 will be displayed in a first orientation to generate a first signal SECG-1. If the first electrode 10 is at a lower elevation or altitude relative to the second electrode, the SECG signal generated from the IMD 8 will be displayed in a second orientation to generate a second signal SECG-2. SECG-2 may a reciprocal image, an inverted image, mirror image, etc. of SECG-1.

Thus, based on the procedure used for implanting the IMD 8 and the orientation of the IMD 8, the resulting SECG signal may be inverted with respect to a traditional surface ECG signal. For example, a traditional ECG signal may match the orientation of that of SECG-1, and thus SECG-2 may have an orientation that is inverted with respect to the orientation of the traditional ECG signal. Typically, the implantation procedure of the IMD 8 is based on the preference of the implanting physician. Some physicians perform an incision at an inferior part of the left chest and implant/insert the IMD 8 in a superior direction or orientation, whereas others create a higher incision and insert the IMD 8 in an inferior direction or orientation. Based on the procedure and the orientation of the IMD 8, the first electrode 10 may be superior or inferior relative to the second electrode 12, thereby causing the inverting differential of the resulting SECG signals described above. Upon analyzing the SECG signals after implantation of the IMD 8, it may be beneficial for a physician to have the SECG signal displayed in a preferred orientation. This preferred orientation may be the same orientation exhibited by traditional surface ECG signals. Otherwise, the physician may be forced to realize that the SECG signal is inverted and adjust his knowledge and interpreting skills accordingly for correct analysis and/or interpretation of the SECG signal. Thus, it may be beneficial to always, or at least have an option to, record and display the SECG in an orientation that matches the orientation of a traditional surface ECG.

The AM sensor 6 may be a multi-axis AM sensor 6. For example, the AM sensor 6 can include a three-axis AM sensor 6. The AM sensor 6 may be incorporated within the IMD 8 or attached to the IMD 8. The AM sensor 6 can be calibrated to determine the orientation of the IMD 8 by measuring a position of the first electrode 10 relative to a position of the second electrode 12. However, the AM sensor 6 can use reference points other than the first and second electrodes 10, 12 to measure the IMD's 8 orientation. Thus, the AM sensor 6 can use a first reference point and a second reference point, where the reference points can be any structure on the IMD 8 that may correspond to the first electrode 10 and the second electrode 12, respectively. Further, the AM sensor 6 can use multiple sets of reference points to increase accuracy or improve determining orientation.

Figure 2A:
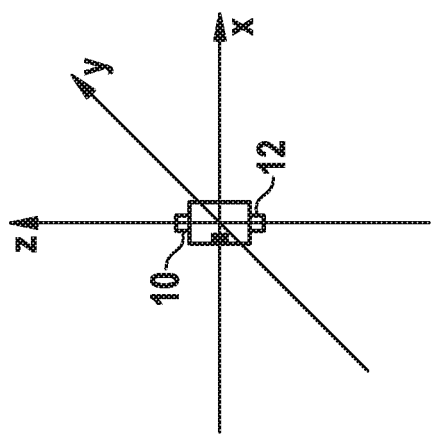
FIGS. 2A-2C show various orientations of the IMD that can be detected with an embodiment of the method, where
Figure 2B:
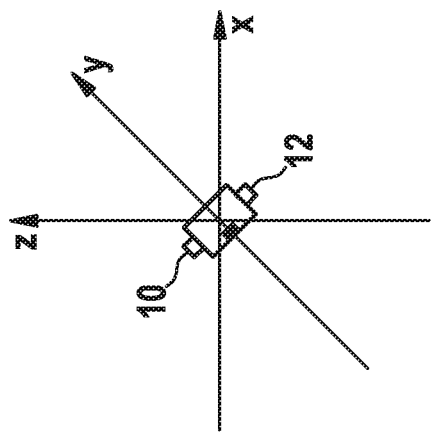
Figure 2C:
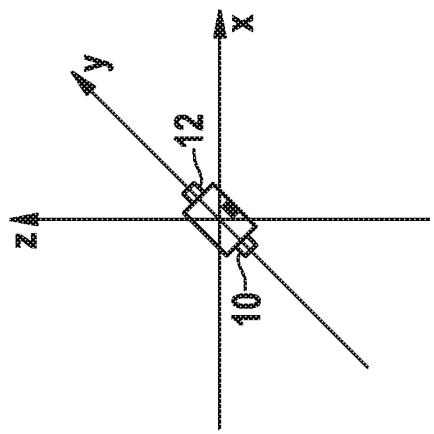

Referring to FIGS. 2A-2C, in some embodiments, the AM sensor 6 can be calibrated to determine the orientation of the IMD 8 by measuring an elevation or an altitude of the first electrode 10 relative to an elevation or an altitude of the second electrode 12. FIG. 2A shows the IMD 8 with the first electrode 10 in a superior position relative to the second electrode 12. FIG. 2B shows the first electrode 10 in a superior position relative to the second electrode 12, but the IMD 8 is seen as being tilted. FIG. 2C shows the first electrode 10 in an inferior position relative to the second electrode 12. As an example, a three-axis AM sensor 8 can detect linear accelerations in an x-direction, a y-direction, and a z-direction. If the IMD 8 is in motion, acceleration and/or deceleration in any of the x-direction, the y-direction, and the z-direction can be calculated and represented by a mathematical vector equation. If the IMD 8 is not in motion, only an acceleration in a negative z-direction or a deceleration in the positive z-direction will be detected due to gravity. Thus, knowing the acceleration in the negative z-direction to be approximately 9.8 m/s$^2$ if the IMD 8 is not in motion, trigonometric algorithms comparing the actual z-direction acceleration to the 9.8 m/s$^2$ can be used to determine if the IMD 8 is tilting, and thus determine the relative elevation or altitude of the first electrode 10 to elevation or altitude of the second electrode 12.

Further components can be used to determine and/or enhance the IMD's 8 orientation measurement, such as inclinometers, gyroscopes, etc. These components can be used in addition to, in the alternative to, and/or incorporated with the AM sensor 6. If the elevation or altitude of first electrode 10 is determined to be higher than the elevation or altitude of the second electrode 12, then the IMD 8 can be deemed to be in an up-orientation (i.e., the first electrode 10 is superior to the second electrode 12). If the elevation or altitude of first electrode 10 is determined to be lower than the elevation or altitude of the second electrode 12, then the IMD 8 can be deemed to be in a down-orientation (i.e., the first electrode 10 is inferior to the second electrode 12). As noted earlier, the IMD 8 in the up-orientation will generate SECG-1 and the IMD 8 in the down-orientation will generate SECG-2.

The system 1 can further include a processor 2 and a non-transitory memory 3, both of which may be in operative communication with the IMD 8, the AM sensor 6, and/or the display 4, where the processor 2 may be programmed to perform the algorithmic functions described herein. The processor 2 can be further programmed to associate the up-orientation with a proxy value of (1) and the down-orientation with a proxy value of (−1); however, other proxy values can be used. Further, each SECG signal can be tagged or coded with the ascertained up-orientation or the ascertained down-orientation when the SECG signal is generated so that the SECG signal can be identified as a SECG-1 signal or a SECG-2 signal. For instance, if an IMD 8 is in the up-orientation then the processor 2 can tag the SECG signals generated therefrom with the proxy value 1 so that each SECG signal is identified as a SECG-1 signal. Similarly, if an IMD 8 is in the down-orientation then the processor 2 can tag the SECG signals generated therefrom with the proxy value (−1) so that each SECG signal is identified as a SECG-2 signal.

It may be predetermined that any one of a SECG-1 and a SECG-2 has an orientation that is the same orientation as that of a traditional ECG signal. For example, it may be predetermined that SECG-1 has the same orientation as that of a traditional ECG signal. Thus, the processor can be further programmed to, upon receiving a SECG-2 signal, perform an inversion function to convert the SECG-2 signal to a SECG-1 signal before being displayed by the display 4. Displaying the signals can be achieved through use of a user interface or other software program programmed to be executed by the processor 2. The inversion function can be generating a reciprocal image, a mirror image, an inverted image, etc. of the SECG-2. Further embodiments can include recording or saving any one of the SECG-1 signal and SECG-2 signal to the non-transitory memory before and/or after any conversions take place.

While it has been disclosed for the SECG-2 signals to be converted to SECG-1 signals, it is understood that SECG-1 signals could be converted to SECG-2 signals. Further, it may be preferred to generate SECG signals that are inverted from the traditional surface ECG signals, or to generate SECG signals to have any other orientation. Thus, the processor 2 can be programmed to convert the SECG signals to any preferred orientation.

One skilled in the art will appreciate that the processor 2 and the non-transitory memory 3 can be part of the IMD 8. Alternatively, or in addition, the processor 2 and the non-transitory memory 3 can be part of an external computing device. Embodiments including use of an external device can receive data from a transceiver or other type of transmitter operatively associated with the IMD 8. The data received can then be manipulated by the external device, which can be done automatically via algorithms and/or manually via a user of the external device. For example, a tagged or coded SECG signal can be transmitted from the IMD 8 to the external device via a live stream in real time. Thus, any one or all of the processors 2 (e.g., a processor of the IMD 8 or a processor 2 of the external device) can perform any of the computational steps described herein, such as, for example, the determining an orientation, converting a SECG signal, etc. Further, any of the processors 2 can be programmed to store any portion of data, before or after being manipulated, on the non-transitory memory 3 associated therewith.

Recording and displaying the generated SECG signal in a known way (i.e., with an orientation matching that of a traditional ECG signal) can be beneficial to a user attempting to interpret signal morphological signals and its variations. In the context of monitoring, the occurrence or progression of cardiac diseases based on changes in signal morphology may be a key attribute of future implantable monitoring devices. Thus, working with known signal orientations of a SECG can not only increase usability, but may also simplify automaticity to monitor and detect disease related changes.

A method for determining an orientation of an IMD 8 can include: 1) attaching or incorporating the AM sensor 6 to the IMD 8, wherein the IMD 8 has a first electrode 10 and a second electrode 12; 2) operatively associating the processor 2 and non-transitory memory 3 with the AM sensor 6 and the display 4; 3) implanting the IMD 8 subcutaneously within a patient to generate SECG signals; 4) determining an orientation of the IMD 8 from the AM sensor 6 measuring an elevation or an altitude of at least one first reference point of the IMD 8 relative to an elevation or an altitude of at least one second reference point of the IMD 8, wherein when the at least one first reference point is superior relative to the at least one second reference point the IMD 8 is in an up-orientation and when the first reference point is inferior relative to the second reference point the IMD 8 is in a down-orientation; 5) associating the up-orientation with a first proxy value and the down-orientation with a second proxy value; 6) tagging each SECG signal with the ascertained up-orientation or down-orientation; 7) identifying each up-orientation generated SECG signal as a SECG-1 signal and identifying each down-orientation generated SECG signal as a SECG-2 signal; determining a preferred orientation before displaying the SECG signals; converting at least one of each SECG-1 signal and SECG-2 signal to generate SECG display signals having the preferred orientation; sending the SECG display signals to the display 4 for viewing, analyzing, and/or recording.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

We claim:

1. A method for determining an orientation of an implantable medical device ("IMD") after being implanted subcutaneously within a patient to generate subcutaneous electrocardiogram ("SECG") signals, wherein the IMD comprising an attached or incorporated acceleration/motion sensor ("AM sensor"), the method comprising:

determining an orientation of the IMD from the AM sensor measuring an elevation or an altitude of at least one first reference point of the IMD relative to an elevation or an altitude of at least one second reference point of the IMD, wherein when the at least one first reference point is superior relative to the at least one second reference point the IMD is in an up-orientation, and when the at least one first reference point is inferior relative to the at least one second reference point the IMD is in a down-orientation;

tagging each SECG signal with the ascertained up-orientation or down-orientation;

determining a preferred orientation for displaying the SECG signals before the SECG signals are displayed;

converting at least one SECG signal to generate a SECG display signal having the preferred orientation; and, displaying the SECG display signal having the preferred orientation.

2. The method recited in claim 1, wherein the IMD has a first electrode and a second electrode.

3. The method recited in claim 2, wherein the first electrode is located at an end of the IMD that is an opposite end at which the second electrode is located.

4. The method recited in claim 2, wherein the at least one first reference point is associated with the first electrode and the at least one second reference point is associated with the second electrode.

5. The method recited in claim 1, wherein the AM sensor is a three-axis acceleration/motion sensor.

6. The method recited in claim 1, wherein the step of converting the at least one SECG signal to generate the SECG display signal haVing the preferred orientation comprises an inversion function performed on the SECG signal.

7. The method recited in claim 1, further comprising use of at least one of an inclinometer and a gyroscope for the determining the orientation of the IMD.

8. The method recited in claim 1, wherein the IMD is an implantable cardiac monitor ("ICM").

9. A method for determining an orientation of an implantable medical device ("IMD") after being implanted subcutaneously within a patient to generate subcutaneous electrocardiogram ("SECG") signals, wherein the IMD comprising an attached or incorporated acceleration/motion sensor ("AM sensor"), the method comprising:

operatively associating a processor and a non-transitory memory with the AM sensor and a display;

determining an orientation of the IMD from the AM sensor measuring an elevation or an altitude of at least one first reference point of the IMD relative to an elevation or an altitude of at least one second reference point of the IMD, wherein when the at least one first reference point is superior relative to the at least one second reference point the IMD is in an up-orientation, and when the at least one first reference point is inferior relative to the at least one second reference point the IMD is in a down-orientation;

tagging each SECG signal with the ascertained up-orientation or down-orientation;

determining a preferred orientation for displaying the SECG signals before the SECG signals are displayed;

converting at least one SECG signal to generate a SECG display signal having the preferred orientation; and, displaying the SECG display signal having the preferred orientation.

10. The method recited in claim 9, further comrpising associated the up-orientation with a first proxy value and the down-oriented with a second proxy value.

11. The method recited in claim 10, further comprising identifying each up-orientation generated SECG signal as a SECG-1 signal and identifying each down- orientation generated SECG signal as a SECG-2 signal.

12. The method recited in claim 11, wherein the step of converting the at least one SECG signal further comprises converting at least one of each SECG-1 signal, and SECG-2 signal to generate the SECG display signal haVing the preferred orientation.

13. The method recited in claim 9, wherein the step of displaying the SECG display signal further comprises sending the SECG display signal to the display.

14. The method recited in claim 9, wherein the IMD has a first electrode and a second electrode.

15. The method recited in claim 14, wherein the first electrode is located at an end of the IMD that is an opposite end at which the second electrode is located.

16. The method recited in claim 14, wherein the at least one first reference point is associated with the first electrode and the at least one second reference point is associated with the second electrode.

17. The method recited in claim 9, wherein the AM sensor is a three- aXis acceleration/motion sensor.

18. The method recited in claim 9, wherein the converting the at least one SECG signal to generate the SECG display signal having the preferred orientation comprises an inversion function performed on the SECG signal.

19. The method recited in claim 9, further comprising use of at least one of an inclinometer and a gyroscope for the determining the orientation of the IMD.

20. The method recited in claim 9, wherein the IMD is an implantable cardiac monitor.

21. A method for determining an orientation of an implantable medical device ("IMD") after being implanted subcutaneously within a patient to generate SECG signals, wherein:

the IMD has an attached or incorporating an acceleration/motion sensor ("AM sensor");

the IMD has a first electrode and a second electrode, wherein the first electrode is located at an end of the IMD that is an opposite end at which the second electrode is located; and wherein the AM sensor is a three-axis acceleration/motion sensor capable of communicating with a processor in operative association with a non-transitory memory and a display, the processor programmed to cause the display to display subcutaneous electrocardiogram ("SECG") signals;

the method comprising:

determining an orientation of the IMD from the AM sensor measuring an elevation or an altitude of the first electrode relative to an elevation or an altitude of the second electrode, wherein when the first electrode is superior relative to the second electrode the IMD is in an up-orientation, and when the first electrode is inferior relative to the second electrode the IMD is in a down-orientation;

tagging each SECG signal with the ascertained up-orientation or down-orientation;

determining a preferred orientation for displaying the SECG signals before the SECG signals are displayed;

converting at least one SECG signal to generate a SECG display signal having the preferred orientation; and, displaying the SECG display signal having the preferred orientation.

22. The method recited in claim 21, further comprising use of at least one of an inclinometer and a gyrooscope for the determining the orientation of the IMD.

23. The method recited in claim 21, wherein the IMD is an implantable cardiac monitor.

* * * * *